July 4, 1950 F. MEILLAND Plant Pat. 960
ROSE PLANT
Filed April 4, 1949
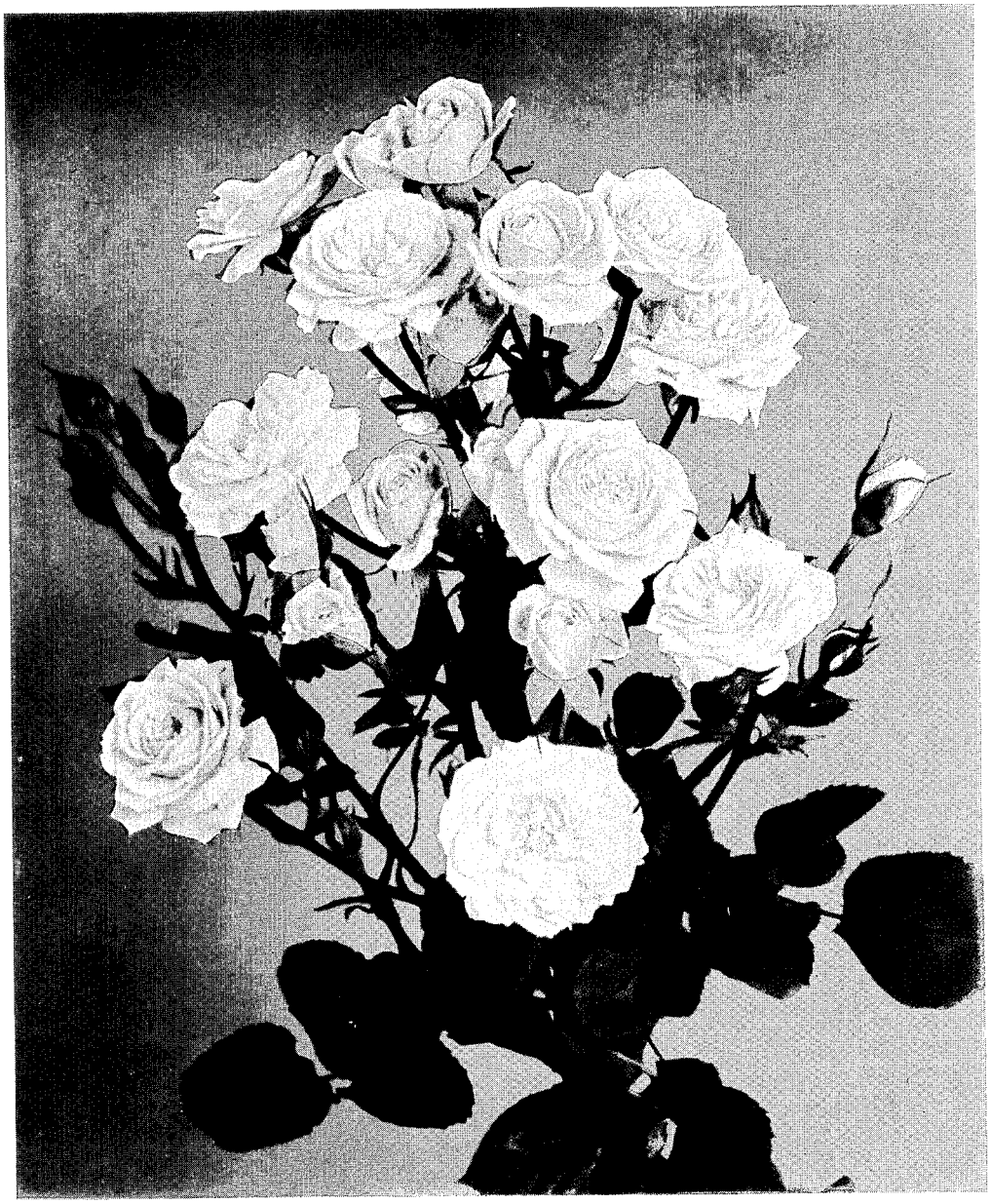
Inventor
F. Meilland
By Robb & Robb
by H C Robb
Attorneys Patented July 4, 1950

UNITED STATES PATENT OFFICE

960

ROSE PLANT

Francis Meilland, Cap Azura, Cap d'Antibes, France, assignor to The Conard-Pyle Company, West Grove, Pa., a corporation of Pennsylvania Application April 4, 1949, Serial No. 85,399

1 Claim. (Cl. 47—61)

The present invention relates to a new and distinct variety of rose plant which is excellent for use as cut flowers and garden decoration in view of its unusual characteristics of growth habit and manner of bearing of its flowers.

More specifically, this new variety is unlike any other of which I am aware in respect of the combination of its dominating characters; that is to say, the plant is strong, bushy, produces good foliage and is so very floriferous that the flowers almost cover the plant like a pink mantle. At the same time, as will appear from the accompanying illustration, the plant is unusually compact in form, enhancing its utility for garden decoration.

Asexual reproduction of this new variety by budding at Tassin-les-Lyon, Rhone, France, and at West Grove, Pennsylvania, shows the foregoing characteristics come true to form and are established.

In the accompanying drawing is illustrated a specimen of the new variety plant, showing particularly the floriferous characteristic of the blossoms above referred to, the cluster effect thereof, and the development of the bloom from bud to full blown flower, all in association with the foliage mantled by the said blooms.

The following is a detailed description of the new variety, all reference to color being in accordance with Ridgway's Color Standards and Nomenclature:

Type: Hardy; bush; outdoor; seedling; for cut flowers and garden decoration.
Class: Polyantha.
Breeding: Seedling. "Pinocchio" (Pl. Pat. No. 484) × "Mme. Jules Gouchault" (unpatented).
Propagation: Holds its distinguishing characteristics through succeeding propagations by budding.

*Flower*

Locality where grown: West Grove, Pennsylvania.
Flowers borne: Infrequently singly, usually several, to stem; on normally strong medium length stems.
Quantity of bloom: Free to abundant outdoors.
Continuity: Continuous.
Fragrance: Penetrating.
Bud:

*Peduncle.*—Medium length; medium heavy; erect; stiff; medium rough; medium red brown prickles. Color — Yellowish Oil Green, Plate V.

*Before calyx breaks.* — Size — medium. Form—pointed; ovoid; with foliaceous appendages on the surface of the bud; with slender entire foliaceous parts extending beyond the tip of the bud equal to one-fourth or more of its length.

*As calyx breaks.*—Color—Spinel Pink, Plate XXVI.

*As first petal opens.* — Size — medium. Form — pointed. Color — outside: Spinel Pink, Plate XXVI; inside: Spinel Pink, Plate XXVI.

*Opening.*—Opens up well.

Bloom: Size, when fully open—medium; 2 inches to 2½ inches.

*Petalage.*—Double; from 35 to 40 petals arranged regularly.

*Form.*—Very high center at first; becoming high centered; inner petals at first very tightly cupped inward with outer petals loosely cupped outward; becoming later, at maturity, very loosely rolled outward.

Petals: Leathery; with inside and outside satiny.

*Shape.*—Outside—round to obovate. Intermediate—obovate. Inside—obovate.

This description of a newly opened flower was made from a rose grown outdoors in the month of August, at West Grove, Pennsylvania:

*Color.* — *Outside petal* — Outside surface: Spinel Pink, Plate XXVI; inside surface: shading from Thulite Pink, Plate XXVI, near base to Spinel Pink, Plate XXVI, over most of petal surface. *Intermediate petal*—outside surface: Spinel Pink, Plate XXVI; inside surface: shading from Thulite Pink, Plate XXVI, near base to Spinel Pink, Plate XXVI, over most of the petal. *Inner petal*—outside surface: Spinel Pink, Plate XXVI; inside surface: Spinel Pink, Plate XXVI.

This description was made from a rose that was open for three days outdoors in the month of August, at West Grove, Pennsylvania:

*Color.*—*Outside petal*—outside surface: Spinel Pink, Plate XXVI; inside surface: shading from Thulite Pink, Plate XXVI, near base to Rose Color, Plate XII, and to Spinel Pink, Plate XXVI. *Inside petal*—outside surface: Spinel Pink, Plate XXVI; inside surface: Deep Rose Pink, Plate XII, occasionally tinged with Spinel Pink, Plate XXVI.

*General color effect.*—Newly opened flower —Spinel Pink, Plate XXVI. Three days open—Deep Rose Pink, Plate XII.

*Behavior.*—Drop off cleanly.

*Flower longevity.*—Cut roses grown outdoors kept at living-room temperatures, four to five days in August.

*Reproductive Organs*

Stamens: Medium number; most arranged regularly about pistils, a few mixed with petaloids.

Filaments: Medium length; most with anthers. Color—Barium Yellow, Plate XVI.

Anthers: Medium size; all open at once; occasionally an anther fused with a petaloid. Color—Orange-Buff, Plate III.

Pollen: Moderately abundant. Color—Cadmium Yellow, Plate III.

Pistils: Medium number.

Styles: Uneven; medium length; medium heavy; separated.

Stigma: Color—Pale Orange Yellow, Plate III.

Ovaries: Some protruding from calyx.

Hips: Short; ovoid; moderately hairy; walls thin. Color—Grass Green, Plate VI.

Sepals: Permanent; moderately long; spear-shaped.

Seeds: Very few; small.

*Plant*

Foliage:

*Leaves.*—Compound of five or seven leaflets; abundant; small to medium; leathery.

*Leaflets.*—Shape, round to oval with apex acute; base round; margin simply serrate.

*Color.*—*Mature*—upper surface: Hellebore Green, Plate XVII; under surface: Asphodel Green, Plate XLI. *Young*—upper surface: Dark Mineral Red, Plate XXVII; occasionally with very small patches of Deep Grape Green, Plate XLI; under surface: Mineral Red, Plate XXVII.

*Rachis.* — Medium heavy. Upper side: grooved; very slightly prickly; under side: very sparsely thorny.

*Stipules.*—Medium length; medium width; medium length points turning out at an angle of less than 90°.

Disease: Resistant to mildew and blackspot.

Growth:

*Habit.*—Bushy; upright; much branched.

*Growth.*—Free.

*Canes.*—Medium heavy.

*Main stems.*—Color, gray-green. *Thorns*—few; short; hooked downward; with short oval base. *Prickles and hairs*—none.

*Branches.*—*Color*, gray-green. *Thorns*—very few; short; hooked downward; with short oval base. *Prickles and hairs*—none.

*New shoots.*—Color, Courge Green, Plate XVII. *Thorns*—few; medium length; hooked downward; with short to medium narrow base. *Prickles and hairs*—none.

I claim:

A new and distinct variety of rose plant of the polyantha class, characterized as to novelty by its strong and bushy habits of growth with good foliage, its compact form and the unusually heavy production of pink flowers to the extent of practically covering the plant like a mantle, substantially as shown and described.

FRANCIS MEILLAND.

No references cited.